United States Patent [19]
Semrad

[11] Patent Number: 4,986,810
[45] Date of Patent: Jan. 22, 1991

[54] TOGGLE CATHETER

[76] Inventor: Neal Semrad, 2180 Cedarhurst Dr., Los Angeles, Calif. 90027

[21] Appl. No.: 402,487

[22] Filed: Sep. 1, 1989

[51] Int. Cl.$^5$ .............................................. A61M 5/32
[52] U.S. Cl. ..................................... 604/106; 604/175
[58] Field of Search ................. 604/93, 104, 106, 164, 604/174, 175, 177, 280, 264

[56] References Cited

U.S. PATENT DOCUMENTS

| | | | |
|---|---|---|---|
| 3,039,468 | 6/1962 | Price | 604/164 X |
| 3,717,151 | 2/1973 | Collett | 604/106 |
| 3,896,804 | 7/1975 | Ekbladh et al. | 604/174 |
| 4,043,346 | 8/1977 | Mobley et al. | 604/107 |
| 4,114,618 | 9/1978 | Vargas | 604/164 |
| 4,571,241 | 2/1986 | Christopher | 604/104 |
| 4,645,493 | 2/1987 | Ferrando et al. | 604/174 |
| 4,737,141 | 4/1988 | Spits | 604/28 |
| 4,826,481 | 5/1989 | Sacks et al. | 604/54 |

Primary Examiner—John D. Yasko
Assistant Examiner—Adam J. Cermak
Attorney, Agent, or Firm—Wagner & Middlebrook

[57] ABSTRACT

An improved catheter comprising a tubular body of flexible material designed for medical use and insertion into a body cavity. The catheter includes at least one opening towards the distal end for the drainage of fluids or their introduction or for monitoring pressures from the body cavity and at least one integral, flexible wing member attached to the outer wall of the catheter and flexible to extend outward and bear against the inner wall of the body cavity to be served by the catheter. In the preferred embodiment, two oppositely located wings are formed integrally into the catheter. An insertion and withdrawal tube is dimensioned to slide over the catheter and hold the wings close against the outer wall of the catheter to facilitate introduction and removal from a body cavity. The distal end of the tube is tapered to aid in deforming the wings into the catheter aligned retracted position.

7 Claims, 2 Drawing Sheets

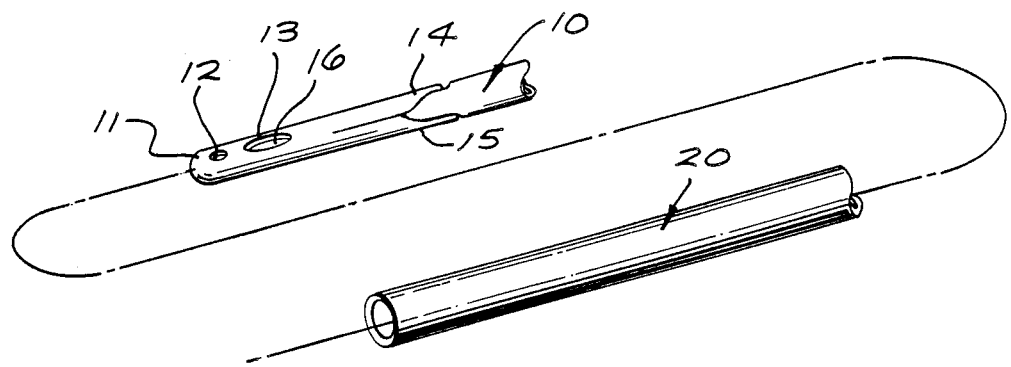
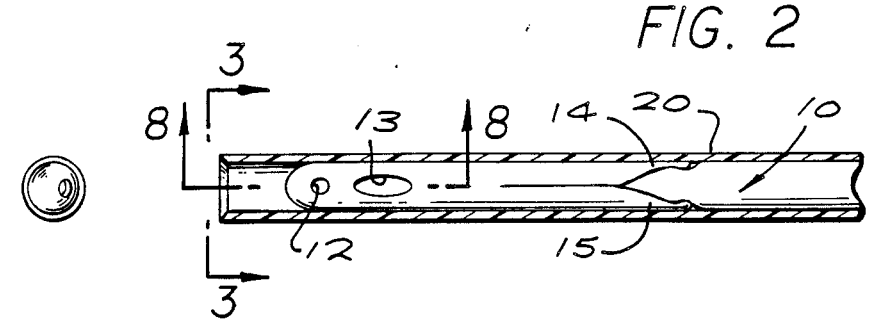
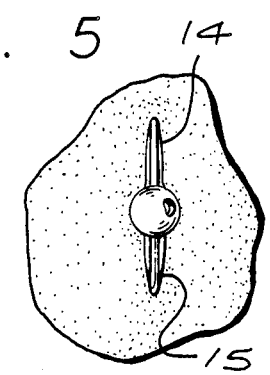
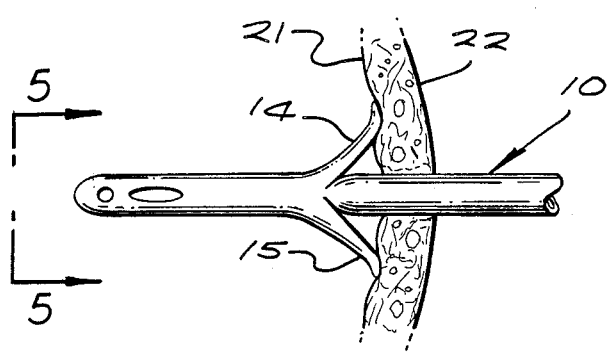
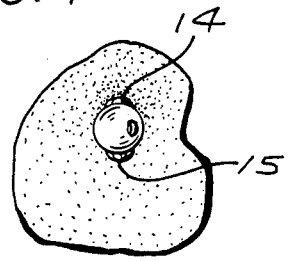
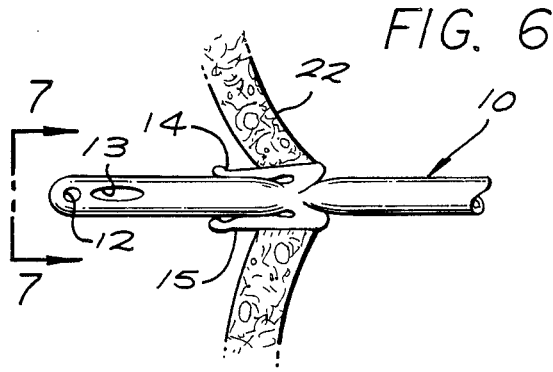

TOGGLE CATHETER

BACKGROUND OF THE INVENTION

In recent years, the use of the catheter has expanded greatly from its classic application for draining fluids from body cavities. An improved catheter guide wire system is disclosed in my co-pending application, Ser. No. 07-402,343, filed Sept. 1, 1989, which allows the use of a catheter with minimum risk of perforation of a back wall of the cavity sought to be drained. The device of my co-pending application expands the applicability of catheters.

In my review of existing catheters for conventional cavity drainage, I have discovered that one serious limitation seems to be inherent in all available catheters, namely, the lack an effective means for maintaining the catheter in place. Surgical tape secured to the skin of the patient and surrounding the catheter is the age-old technique used. Likewise, the Foley-type catheter for urinary bladder drainage has been available for years but is designed specifically for trans-urethral (a natural body opening with epithelial lining) insertion and withdrawal. In the case of uncooperative or unconscious patients, the unplanned withdrawal of a catheter through its entrance hole is an unfortunate common occurrence. Unwanted migration of cavity fluids, possibility of infection and the like are possible under these circumstances.

Having placed many catheters with continuing concern, it appeared to me that some type of self-holding catheter was an absolute necessity.

BRIEF DESCRIPTION OF THE INVENTION

Faced with the state of the art, it appeared to me that some integral holding device for the catheter could be developed. Since it is the physician's desire to maintain the catheter within the body cavity, and body cavities usually have a fairly firm wall, a device which temporarily uses the inner wall of the body cavity for securement would provide a high degree of reliability. Likewise, secured within the cavity, movement of the arms or surface of the patient cannot contact the basic catheter holding device.

I am familiar with the standard toggle bolt used in residential and commercial installations of screws and other fixtures in hollow walls. Toggle bolts, as such, are well established as reliable holders. A major distinction exists however between the hardware toggle bolt and the medical catheter, in that the medical catheter must not only be inserted through a minimum size opening and must hold reliably, but also must be removed with minimum disturbance of the cavity wall and with minimum possibility of flow of residual fluid from the body cavity and, most important, minimum possibility of infection.

The catheter cannot be removed in a manner which produces any significant or additional cutting or tearing of tissue. In the case of the medical catheter, the patients body must be able to reasonably mend the catheter entrance point with a minimum scar.

Given these additional considerations, it appeared to me that a flexible catheter, having a pair of integral wings or toggles, is a candidate for an effective self-holding catheter. The wings must add minimum or no additional diameter or transverse dimension to the catheter to facilitate entrance to the body cavity through the cavity wall and must be configured to automatically expand within the cavity and provide a pair of holding legs against the inner wall of the cavity during the catheter placement and operation. The wings also must provide a degree of flexibility so that they can be folded inwardly to allow the catheter to be withdrawn, either by direct pulling at a force level determined by the placing physician, or through the use of a withdrawal tube. The wings for most applications must not separate from the catheter tube nor restrict flow through the catheter when it is in place.

Each of the foregoing requirements are met by what I term a toggle bolt catheter, one embodiment, which comprises a closed end hollow catheter having one or more fluid entries at its distal end and a fluid passage throughout its length to the exterior of the patient. A pair of rearward extending wings are formed integrally in the wall to ensure a locking expansion against any adjacent wall when the slight outward tug is applied by the catheter when placed in position.

The wings have sufficient flexibility also to allow them to be folded back toward the distal end of the catheter on removal The wings may be configured for fold-back by the cavity wall itself or by engagement with a tapered tube which is placed over the catheter and introduced into the body cavity prior to removal of the catheter

BRIEF DESCRIPTION OF THE DRAWING

This invention may be more clearly understood from the following description and by reference to the drawing, in which:

FIG. 1 is an exploded perspective view of the toggle catheter and withdrawal tube in accordance with this invention;

FIG. 2 is a fragmentary longitudinal sectional view of the withdrawal tube of FIG. 1 with catheter in place;

FIG. 3 is a full end view corresponding to FIG. 2;

FIG. 4 is a side elevational view of the catheter in accordance with this invention in place within a body cavity wall;

FIG. 5 is an elevational view taken in the direction of lines 5—5 of FIG. 4;

FIG. 6 is a side elevational view of the catheter of this invention being withdrawn from a body cavity;

FIG. 7 is a front elevational view taken along in the direction of the arrow 7—7 of FIG. 6;

DETAILED DESCRIPTION OF THE INVENTION

Figure 8:
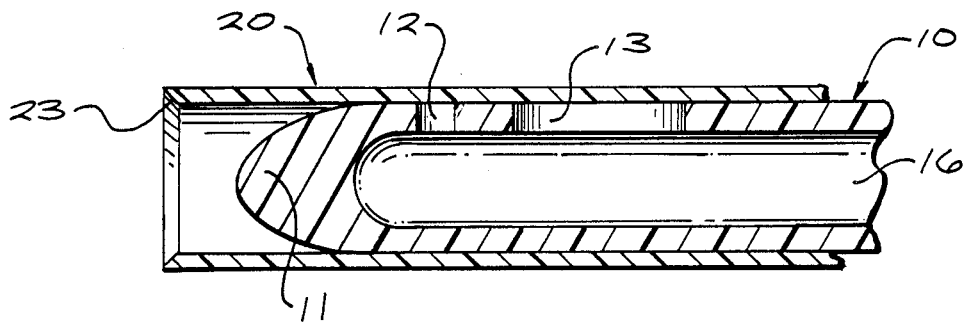
FIG. 8 is an enlarged fragmentary vertical sectional view of a catheter within its withdrawal tube.
Figure 9:
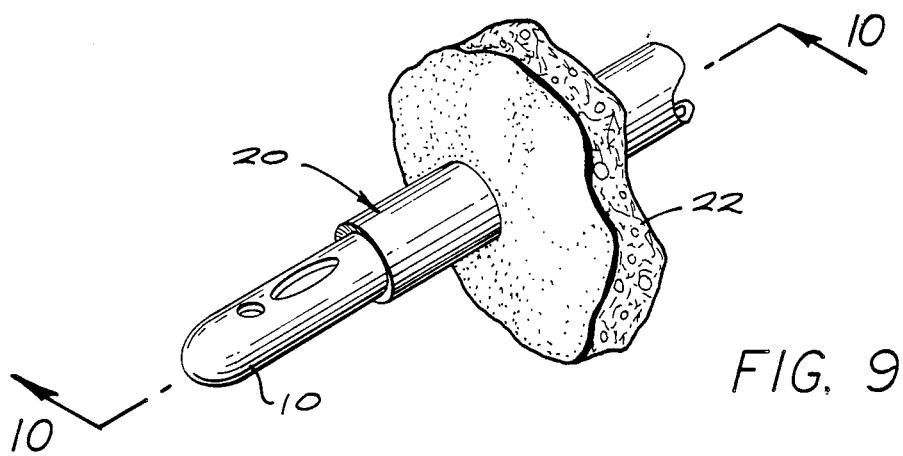
FIG. 9 is a perspective view of the catheter of this invention and withdrawal tube extending through the body cavity wall.

Now referring to FIG. 1 in connection with FIGS. 2 and 3 wherein a catheter, generally designated 10, may be seen as including a distal end 11 having one or more openings 12 and 13 with a plurality, for example, two integral wings 14 and 15, which, in their normal reposed position, are attached to the body of the catheter 10 toward its distal end with the wings 14 and 15 laying along the body extending away from the distal end. The catheter 10 is hollow, having a longitudinal opening 16 through which body cavity fluids may be withdrawn when the catheter 10 is in place.

Shown adjacent to the catheter 10, is a tube 20, having its inside diameter correlated with the outside diameter with the catheter 10, so that the catheter 10 will slip easily into tube 20 in a near fluid tight relationship. The tube 20 may be used to aid in both the insertion and the withdrawal of the catheter 10. When used for insertion, a stop guide wire of the type disclosed in my co-pending application referenced above, may first be inserted with its obturator and the tube 20 slid over the stop guide wire into the body cavity, the obturator and guide wire removed by drawing them out through tube 20 to be replaced by the distal end of the catheter 10 of FIG. 1. The tube 20 is then removed, leaving the distal end of the catheter 10 with its wings 14 and 15 within the body cavity. A slight pressure applied to the proximal end of the catheter 10 outside of the patient causes the wings 14 and 15 of the catheter 10 to spread against the inner wall 21, inner surface of the body cavity wall 22, as illustrated in FIGS. 4 and 5.

As shown in the drawing, two wings 14 and 15 are used, however it is recognized that conceivably a single wing might provide sufficient locking and that three wings, equally spaced around the periphery, should give better locking in the body cavity. In my view, a dual wing catheter provides adequate holding and greater mobility within the body cavity which may be desirable to bring the one or two openings into the most effective cavity draining position.

The catheter 10 may be withdrawn in certain situations employing the method illustrated in FIGS. 6 and 7. For example, when the body cavity is a stomach, bladder or chest cavity, the wall 22 of the cavity provides sufficient tissue strength to allow the catheter to be removed by a gentle but firm pressure applied to the proximal end of the catheter 10 causing the wings 14 and 15 to fold back toward the distal end compressing into the tube to a variable degree with a temporary and minimal stretching of the opening in the body cavity wall 22 to allow the folded wings 14 and 15 to pass through the wall 22 and out of the patient's body. The relative size of the wings 14 and 15 during withdrawal in FIG. 7 is apparent when compared with their in place position in FIG. 5.

An alternate method of removal of the catheter 10 is illustrated in FIGS. 8-11. In FIG. 8, catheter 10 is located within the tube 20 and clearly shows the distal end 11, its openings 12 and 13 as well as its central drain opening 16. When the catheter 10 is located within the tube 20, the catheter 10 and tube 20 act as a single member with hardly any increase in diameter of the opening in the cavity wall 22 of FIGS. 9 and 10. The distal end of the tube 20 is shown to have a taper 23 from the outer edge inward. The taper 23 aids in the folding of the wings 14 and 15 as is more apparent in FIG. 10.

Figure 10:
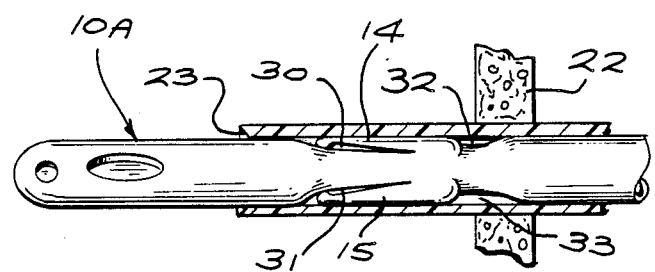
FIG. 10 is a partial longitudinal sectional view corresponding to FIG. 9.
Figure 11:
FIG. 11 is a fragmentary enlarged view of the end detail of the withdrawal tube of this invention.

In the embodiment of this invention shown in FIG. 10, the catheter 10A has similar wings 14 and 15, however, the inboard area of catheter 10A adjacent to the wings 14 and 15 is necked down, if needed, depending on the wall thickness desired, in the areas 30 and 31 to aid in clearance of the wings during withdrawal. Similarly, the catheter 10A is necked down in the area 32 and 33 to provide a recess for the wings 14 and 15 when in their normal position ready for insertion in the body cavity. I have found that medical grade polyethylene is a suitable material for the catheter 10. The diameter and stiffness will vary with the particular body cavity intended to be penetrated. Below are examples of size and stiffness recommended.

| PROCEDURE OR BODY CAVITY | CATHETER DIAMETER | | STIFFNESS |
|---|---|---|---|
| | O.D. | I.D. | |
| Stomach | 1-2 cm | .8-1.8 cm | similar to naso-gastric tube |
| Urinary bladder (percutaneous) | 3 mm (pediatric) | 2 mm | similar to trans-urethral catheter |
| | 2.5 cm (3-way adult) | 2.3 cm | |
| Gall bladder (percutaneous) | 2 mm-1.5 cm | 1 mm-1.4 cm | soft |
| Kidney | 2 mm-2 cm | 1.5 mm-1.5 + cm | very flexible |
| Abscess cavity | 2 mm-2 cm | 1.5 mm-1.5 + cm | very flexible |
| Pericardial cavity | 2 mm-2 cm | 1.5 mm-1.5 + cm | very flexible |
| Pleural cavity | .25 cm-3 cm | 1.5-2.8 cm | similar to softest chest tube see U.S. Pat. No. 4,813,929 |
| Central Nervous System (ventricle) | 2 mm-1 cm | 1 mm-1.9 cm | soft to stiff depending on placement within tissue |
| Central Nervous System (peri-spinal cord) | 2-4 mm | 1.6-3.6 mm | very soft and flexible |
| Central Nervous System (epidural) | 2-4 mm | 1.6-3.6 mm | very soft and flexible |

The tube 20 is preferably medical grade polyethylene and varies in diameter and length to match its catheter 10 or 10A. The length of the tube 20 will vary with the application from 15 to 30 centimeters.

The foregoing constitute the best mode known by the applicant for carrying out this invention, however the specific embodiments disclosed are illustrative of the principle of the invention and are not limiting in its scope. To the contrary, it is recognized that one of ordinary skill in the art, given this teaching, may make variations in the structure or compositions without departing from the spirit and scope of this invention. Its scope is defined by the following claims including the protection offered by the doctrine of equivalents.

What is claimed is:

1. A catheter comprising:

an elongated hollow member having a distal end region including at least one inlet positioned to allow entrance of body fluids into the interior of the elongated hollow member and an outlet in a proximal end region opposite of said distal end region for draining of body fluids from a body cavity;

said inlet being located in the distal end region of said catheter;

at least one flexible, laterally extendable wind member unitary with and on the exterior of said catheter for retaining the catheter within a body cavity by extension of the wing member against the inner wall of the body cavity;

said wing member being attached to said catheter toward the distal end thereof but proximal to said inlet and foldable toward the proximal end thereof upon insertion of the catheter into the body cavity and foldable toward the distal end of said catheter upon withdrawal of the catheter from the body cavity.

2. The catheter in accordance with claim 1 including at least one additional wing member spaced radially from the first mentioned wing member and generally in the same longitudinal position with respect to the first mentioned wing member for providing a two-positioned stop for bearing against spaced areas of the wall of a body cavity into which the catheter is inserted.

3. The catheter in accordance with either claim 1 or claim 2 wherein the wall of said catheter includes at least one recess for each such wing member to allow the wing member to fold generally into the catheter during insertion or withdrawal of the catheter from the body cavity.

4. The combination in accordance with claim 1 or claim 2 wherein each wing member includes an attachment portion joining the wing member to the outside wall of said catheter and wherein said catheter includes a recess in the outside wall for each wing member extending from the attachment portion of the wing member toward the distal end of said catheter.

5. The combination in accordance with claim 1 or claim 2 wherein each wing member includes an attachment portion joining the wing member to the outside wall of said catheter and wherein said catheter includes a recess in the outside wall for each wing member extending from the attachment portion of the wing member away from the distal end of the catheter.

6. The catheter tube combination in accordance with claim 1 including a placement tube dimensioned with an inside measurement corresponding substantially to the outside measurement of the catheter.

7. The catheter tube combination in accordance with claim 6 wherein said tube member includes an outer surface and an inner surface and an open distal end; said open distal end having a taper from the outer surface toward the inner surface for aiding in folding the wing members of the catheter as the tube is inserted over the catheter.

* * * * *